United States Patent
Gruber et al.

(10) Patent No.: US 8,769,841 B2
(45) Date of Patent: Jul. 8, 2014

(54) LYOPHILISATION TARGETING DEFINED RESIDUAL MOISTURE BY LIMITED DESORPTION ENERGY LEVELS

(71) Applicant: Octapharma AG, Lachen (CH)

(72) Inventors: Gerhard Gruber, Vienna (AT); Anton Reschny, Vienna (AT)

(73) Assignee: Octapharma AG, Lachen (CH)

( * ) Notice: Subject to any disclaimer, the term of this patent is extended or adjusted under 35 U.S.C. 154(b) by 0 days.

(21) Appl. No.: 13/625,482

(22) Filed: Sep. 24, 2012

(65) Prior Publication Data

US 2013/0118025 A1 May 16, 2013

Related U.S. Application Data

(63) Continuation of application No. 11/812,512, filed on Jun. 19, 2007, now abandoned.

(60) Provisional application No. 60/818,339, filed on Jul. 5, 2006.

(30) Foreign Application Priority Data

Jun. 20, 2006 (EP) .................................. 061157363

(51) Int. Cl.
*F26B 5/00* (2006.01)

(52) U.S. Cl.
USPC ....... 34/287; 435/252.3; 424/185.1; 530/330; 560/322

(58) Field of Classification Search
USPC ................ 34/284, 287, 92; 435/6, 69.1, 199, 435/252.3; 424/185.1, 142.1; 530/330, 530/388.15; 560/322; 536/23.1
See application file for complete search history.

(56) References Cited

U.S. PATENT DOCUMENTS

| | | | |
|---|---|---|---|
| 2,695,285 A | 11/1954 | Philip et al. | |
| 2,882,270 A | 4/1959 | Isidoro et al. | |
| 2,929,150 A * | 3/1960 | Johnston | ......................... 34/338 |
| 3,034,968 A | 5/1962 | Johnston | |
| 3,228,838 A | 1/1966 | Rinfret et al. | |
| 3,269,025 A | 8/1966 | Dryden et al. | |
| 3,269,905 A | 8/1966 | Alder et al. | |
| 3,281,954 A | 11/1966 | Baer et al. | |

(Continued)

FOREIGN PATENT DOCUMENTS

| | | | | |
|---|---|---|---|---|
| CN | 102584982 | * | 7/2012 | ........... C07K 14/605 |
| DE | 10 2010 008981 | * | 8/2011 | ............ A61K 31/80 |

(Continued)

OTHER PUBLICATIONS

Extended European Search Report dated Nov. 29, 2006, issued in European Patent Application No. 06115736.8.

(Continued)

*Primary Examiner* — Steve M Gravini
(74) *Attorney, Agent, or Firm* — Venable LLP; Nancy J. Axelrod; Michael A. Gollin

(57) ABSTRACT

A process of freeze drying of an essentially aqueous solution comprising at least one first step having a first temperature and pressure level (i.e. primary drying phase) and at least one second step having a second temperature and pressure level (i.e. secondary drying phase) following the first step, wherein in the secondary drying phase limited desorption energy input is applied.

9 Claims, 2 Drawing Sheets

(56) References Cited

U.S. PATENT DOCUMENTS

| | | |
|---|---|---|
| 3,289,314 A | 12/1966 | Paolo |
| 3,292,271 A | 12/1966 | Hopkins et al. |
| 3,384,979 A | 5/1968 | Leine et al. |
| 3,428,584 A | 2/1969 | Riley |
| 3,431,655 A * | 3/1969 | Ganiaris et al. .................. 34/287 |
| 3,440,732 A | 4/1969 | Vanderpool et al. |
| 3,516,935 A | 6/1970 | Monforte et al. |
| 3,532,506 A | 10/1970 | Morand et al. |
| 3,541,805 A | 11/1970 | Kumar et al. |
| 3,567,520 A | 3/1971 | Dennery et al. |
| 3,579,360 A | 5/1971 | Rey et al. |
| 3,607,858 A | 9/1971 | Querry et al. |
| 3,620,776 A | 11/1971 | Abraham Rudolph Mishkin et al. |
| 3,633,283 A | 1/1972 | Mishkin et al. |
| 3,638,327 A | 2/1972 | Levy et al. |
| 3,673,698 A | 7/1972 | Guerard |
| 3,685,163 A | 8/1972 | Olt |
| 3,703,772 A | 11/1972 | McHugh et al. |
| 3,716,382 A | 2/1973 | Chandrasekaran et al. |
| 3,731,391 A | 5/1973 | Schweizer |
| 3,732,627 A | 5/1973 | Wertheim |
| 3,743,714 A | 7/1973 | Deutsch |
| 3,759,047 A | 9/1973 | King, III et al. |
| 3,855,712 A | 12/1974 | Blonde |
| 3,862,302 A | 1/1975 | Price et al. |
| 3,873,745 A | 3/1975 | Rey et al. |
| 3,879,855 A | 4/1975 | Weiser et al. |
| 3,888,017 A | 6/1975 | McBride |
| 3,888,859 A | 6/1975 | Ponzoni et al. |
| 3,909,957 A | 10/1975 | Passey |
| 3,915,794 A | 10/1975 | Zygraich et al. |
| 3,916,532 A | 11/1975 | Jaeger et al. |
| 3,932,943 A * | 1/1976 | Briggs et al. ..................... 34/287 |
| 3,939,260 A | 2/1976 | Lafon |
| 3,960,476 A | 6/1976 | Ghilardi et al. |
| 3,981,676 A | 9/1976 | Ghilardi et al. |
| 4,001,944 A | 1/1977 | Williams |
| 4,009,328 A | 2/1977 | Mallams et al. |
| 4,016,657 A | 4/1977 | Passey |
| 4,117,603 A | 10/1978 | Smith |
| 4,119,774 A | 10/1978 | Andersson et al. |
| 4,134,214 A | 1/1979 | Graham et al. |
| 4,146,971 A | 4/1979 | Bornstein et al. |
| 4,178,695 A | 12/1979 | Erbeia |
| 4,211,015 A | 7/1980 | Adams et al. |
| 4,223,002 A | 9/1980 | Newman |
| 4,236,321 A | 12/1980 | Palmonari et al. |
| 4,251,923 A | 2/1981 | Kuri |
| 4,286,378 A | 9/1981 | Micheli |
| 4,323,478 A | 4/1982 | Adams et al. |
| 4,329,787 A | 5/1982 | Newton |
| 4,383,376 A | 5/1983 | Numamoto et al. |
| 4,389,422 A | 6/1983 | Hudak |
| 4,470,202 A | 9/1984 | Buxton et al. |
| 4,521,975 A * | 6/1985 | Bailey .............................. 34/285 |
| 4,540,410 A | 9/1985 | Wood et al. |
| H000070 H | 5/1986 | Berkowitz et al. |
| 4,624,868 A | 11/1986 | Muller |
| 4,642,903 A | 2/1987 | Davies |
| 4,712,310 A | 12/1987 | Roy |
| 4,734,116 A | 3/1988 | Ehrsam |
| 4,806,343 A | 2/1989 | Carpenter et al. |
| 4,820,627 A | 4/1989 | McGeehan |
| 4,883,507 A | 11/1989 | Rey et al. |
| 5,044,091 A | 9/1991 | Ueda et al. |
| 5,075,231 A | 12/1991 | Moreau et al. |
| 5,124,452 A | 6/1992 | Gennari |
| 5,164,139 A | 11/1992 | Fujioka et al. |
| 5,169,834 A | 12/1992 | Arendt |
| 5,309,649 A * | 5/1994 | Bergmann et al. ............... 34/284 |
| 5,340,592 A | 8/1994 | Goodrich, Jr. et al. |
| 5,384,124 A | 1/1995 | Courteille et al. |
| 5,650,192 A | 7/1997 | Britton et al. |
| 5,703,225 A | 12/1997 | Shet et al. |
| 5,712,161 A | 1/1998 | Koezuka et al. |
| 5,727,333 A | 3/1998 | Folan |
| 5,767,231 A | 6/1998 | Schull et al. |
| 5,811,031 A | 9/1998 | Jansen et al. |
| 5,911,917 A | 6/1999 | Masters |
| 5,964,043 A | 10/1999 | Oughton et al. |
| 5,996,248 A | 12/1999 | Coppa et al. |
| 6,148,536 A | 11/2000 | Iijima |
| 6,194,079 B1 | 2/2001 | Hekal |
| 6,212,791 B1 | 4/2001 | Thompson et al. |
| 6,308,434 B1 * | 10/2001 | Chickering et al. ............. 34/373 |
| 6,311,409 B1 | 11/2001 | Coppa et al. |
| 6,408,536 B1 | 6/2002 | Deusser et al. |
| 6,560,897 B2 | 5/2003 | Chickering, III et al. |
| 6,627,597 B1 | 9/2003 | Achanta et al. |
| 6,684,524 B1 | 2/2004 | Sennhenn et al. |
| 6,772,537 B2 | 8/2004 | Kawahara |
| 6,787,158 B1 | 9/2004 | Erdmann et al. |
| 6,931,888 B2 | 8/2005 | Shekunov et al. |
| 6,971,187 B1 * | 12/2005 | Pikal et al. ....................... 34/285 |
| 6,984,404 B1 * | 1/2006 | Talton et al. ................... 424/490 |
| 7,007,406 B2 | 3/2006 | Wang et al. |
| 7,073,349 B2 | 7/2006 | Shekunov et al. |
| 7,363,726 B2 | 4/2008 | Wang et al. |
| 2001/0027614 A1 | 10/2001 | Chickering et al. |
| 2002/0056206 A1 | 5/2002 | Pace et al. |
| 2002/0099043 A1 | 7/2002 | Akimoto et al. |
| 2003/0037459 A1 * | 2/2003 | Chickering et al. ............. 34/576 |
| 2003/0119042 A1 | 6/2003 | Franco De Sarabia Rosado et al. |
| 2003/0157241 A1 | 8/2003 | Hossainy et al. |
| 2003/0185894 A1 | 10/2003 | Zenoni et al. |
| 2003/0222364 A1 | 12/2003 | Jackson et al. |
| 2004/0043042 A1 | 3/2004 | Johnson et al. |
| 2004/0060194 A1 | 4/2004 | Kawahara |
| 2004/0154317 A1 | 8/2004 | Shekunov et al. |
| 2004/0237334 A1 | 12/2004 | Kawahara |
| 2005/0080136 A1 | 4/2005 | Watanabe et al. |
| 2005/0100604 A1 | 5/2005 | Shimizu et al. |
| 2005/0160615 A1 | 7/2005 | Wang et al. |
| 2005/0178020 A1 | 8/2005 | Shekunov et al. |
| 2005/0226893 A1 | 10/2005 | Juneau et al. |
| 2005/0232930 A1 | 10/2005 | Richter-Friis et al. |
| 2005/0281737 A1 | 12/2005 | Kuperus et al. |
| 2006/0053652 A1 * | 3/2006 | Gyory et al. ..................... 34/284 |
| 2006/0121489 A1 | 6/2006 | Gorenstein et al. |
| 2006/0130355 A1 | 6/2006 | Wang et al. |
| 2006/0266707 A1 | 11/2006 | Fisher et al. |
| 2006/0288604 A1 | 12/2006 | Mukai et al. |
| 2007/0088057 A1 | 4/2007 | Lunsmann et al. |
| 2007/0186437 A1 * | 8/2007 | Gasteyer et al. ................ 34/287 |
| 2008/0112972 A1 | 5/2008 | Truong-Le |
| 2008/0132408 A1 | 6/2008 | Mitchell et al. |
| 2008/0155853 A1 | 7/2008 | Wang et al. |
| 2008/0172902 A1 * | 7/2008 | Gruber et al. ................... 34/286 |
| 2008/0229609 A1 | 9/2008 | Bronshtein |
| 2008/0276482 A1 | 11/2008 | Broughall et al. |
| 2009/0007931 A1 | 1/2009 | Krebs et al. |
| 2009/0047358 A1 | 2/2009 | Weers et al. |
| 2009/0090022 A1 * | 4/2009 | Ho et al. ......................... 34/406 |
| 2009/0158612 A1 | 6/2009 | Thilly et al. |
| 2009/0223080 A1 * | 9/2009 | McCarthy et al. .............. 34/284 |
| 2010/0011610 A1 * | 1/2010 | Bittorf et al. .................... 34/359 |
| 2010/0018073 A1 * | 1/2010 | Fissore et al. ................... 34/284 |
| 2010/0107436 A1 * | 5/2010 | Velardi et al. ................... 34/284 |
| 2012/0167405 A1 * | 7/2012 | Hubbard et al. ................. 34/82 |
| 2012/0222326 A1 * | 9/2012 | Hubbard et al. ................ 34/201 |
| 2012/0304483 A1 * | 12/2012 | Sirard et al. ..................... 34/289 |
| 2013/0118025 A1 * | 5/2013 | Gruber et al. ................... 34/284 |

FOREIGN PATENT DOCUMENTS

| | | | |
|---|---|---|---|
| EP | 0078225 A1 | 5/1983 | |
| EP | 1870649 A1 | 12/2007 | |
| EP | 1870650 A1 | 12/2007 | |
| EP | 2522996 | * 11/2012 | ............ G01N 33/04 |
| JP | 55-147548 | 11/1980 | |
| JP | 57-007490 | 1/1982 | |
| JP | 57-169425 | 10/1982 | |

(56) References Cited

FOREIGN PATENT DOCUMENTS

WO     WO-03/026786 A2     4/2003
WO     WO 2012/148550     * 11/2012    ............. A61K 31/52

OTHER PUBLICATIONS

International Preliminary Report on Patentability (Chapter I) dated Jan. 20, 2011, issued in International Application No. PCT/IB2007/003503.

Adams, "Freeze-Drying of Biological Materials", Drying Technology, vol. 9, No. 4, pp. 891-925. (1991).

Takamura et al., "Prediction of Chemotherapeutic Response by Collagen Gel Droplet Embedded Culture-Drug Sensitivity Test in Human Breast Cancers", International Journal of Cancer, vol. 98, pp. 450-455. (2002).

Koshida et al., "In Vitro Chemosensitivity Test for Human Genito-Urinary Tumors Using Collagen Gel Matrix", International Journal of Urology, vol. 12, pp. 67-72. (2005).

Costello, "Screening for Tumor Therapy Sensitivity Using an Ex Vivo Invasion Assay", Neuro-Oncology, vol. 8, p. 440, Abstract No. TA-11. (2006).

Costello, "Determination of Human Brain Tumour Therapy Response Using an Ex Vivo Invasion Assay Provides a Potential Step Toward Individualized Treatment", Journal of Clinical Oncology, vol. 24, No. 185, Abstract No. 11509.

* cited by examiner

LYOPHILISATION TARGETING DEFINED RESIDUAL MOISTURE BY LIMITED DESORPTION ENERGY LEVELS

CROSS REFERENCE OF RELATED APPLICATION

This application is a Continuation Application of U.S. Ser. No. 11/812,512, filed Jun. 19, 2007, which claims the benefit of European Application No. 0611573638, filed Jun. 20, 2006 and claims the benefit of U.S. Provisional Application No. 60/818,339, filed Jul. 5, 2006, which are hereby incorporated in their entirety by reference.

BACKGROUND OF THE INVENTION

The invention pertains to a process of freeze drying of an essentially aqueous solution.

Lyophilisation (freeze drying) is a stabilising process in which the formulation is first frozen, i.e., a separation of the solvent and the solutes, and then the concentration of the solvent, mainly water, is reduced first by sublimation (primary drying) and then by desorption (secondary drying) to levels that will no longer support biological growth or chemical reaction. [Lyophilization Seminar Notes, 1993, p. 30]

Within the last decades freeze drying has become the most common method for the preparation of pharmaceuticals which are not adequately stable in solution. Among them the increasing demand for complex organic molecules, peptides and (recombinant) proteins being used as medicinal preparations have been the driving force to more scientifically investigate freeze drying cycles.

Being time consuming and expensive freeze drying is often the rate limiting process in the biopharmaceutical industries. Despite this disadvantage experience has shown that a variety of chemical reactions in aqueous solution, many of which are unacceptable in terms of product safety, are retarded in the dry state (e.g. hydrolysis, disulfide rearrangement, oxidation, aggregation etc.). Hence, freeze drying is considered one of the best methods to preserve proteins yielding products that are stable and convenient to store, ship or handle and which is accepted by the authorities as a suitable process step in the manufacture of therapeutic products.

SUMMARY OF THE INVENTION

As mentioned above, the secondary drying is typically related to desorption of water to target levels that will allow to use and/or store the formulation in a stable state. The secondary drying is usually performed at low chamber pressure and increased shelf temperatures for a distinct (limited) period of time until the target level of water (herein also referred to as residual moisture, RM) is achieved. However, by doing so several prerequisites must be fulfilled. For example, a homogenous temperature distribution of shelves and lyophilisator chamber (no hot/cold spots), a regular contact of vials between each other and between shelf surfaces leading to controlled heat transfer, all vials must be of identical quality (i.e. even thickness of glass wall and bottom), the product must have reached an almost identical physical state within each and every vial, etc. Taken together, since above mentioned prerequisites are hardly under control negative impact on the performance and results of a freeze drying cycle and the product quality thereof cannot be excluded.

In one embodiment of the invention the limited desorption energy input applied results in a desorption rate at the target rest moisture of the product approaching zero.

In another embodiment the process of the invention comprises a first shelf temperature level and a first chamber pressure level (i.e. primary or sublimation drying phase) and at least one second step having a second shelf temperature level and a second chamber pressure level (i.e. secondary or desorption drying phase) following the first step, characterized in that in the secondary or desorption drying phase at which the desorption rate at the target at rest moisture of the product approaches zero.

The "secondary drying (SD) phase" of a freeze drying cycle is per definition characterised by desorption i.e. removal of bound water. Although some other freeze drying parameters (e.g. chamber pressure, condenser temperature, etc.) applied during secondary drying must be considered the shelf temperature is the driving force for desorption (or the desorption rate if the amount of desorbed water in percent of solids per time [%/h] is calculated).

From the desorption rate the amount of desorbable water can be calculated at a given time point as follows:

$$dWt = \int_{t=0}^{t=1} DR\,dt$$

Desorbable water represents the amount of water still present in the product that can be removed by desorption. This must however not necessarily represent the identical amount of water that is determined by e.g. Karl Fischer titration or gravimetric methods for rest moisture determination since not all water present in a product can be removed by desorption.

By measuring the pressure increase during SD (i.e. close the valve between chamber and condenser for a defined period of time; so called "pressure rise measurement") the desorption rate and consequently the desorbable water dW can be estimated.

The dW and the corresponding rest moisture of a given substance must, however, be empirically estimated for every individual product due to above mentioned discrepancy between desorbable water and rest moisture determination. The desired dW value (corresponding to the desired rest moisture content) can afterwards be set as a process lead parameter at which predefined level the SD is terminated).

By keeping other freeze drying parameters constant (e.g. chamber pressure, condenser temperature) the desorption rate at a given shelf temperature decreases and approaches zero. In other words, even after extended SD time a certain, constant rest moisture content of the product will be approached. By determination of rest moisture levels after SD at different shelf temperatures a particular shelf temperature (or shelf temperature range) can empirically be defined where the corresponding rest moisture of the product reaches the targeted value and remains almost constant even in case of an extended SD phase.

This is in contrast to commonly applied freeze drying processes where the SD must be terminated or is automatically terminated by time.

Surprisingly it was found that the residual moisture could be targeted by adjusting the shelf temperature to levels even below temperature levels selected for primary drying. This method (i.e. the adjustment of the shelf temperature correlating with a limited level of desorption energy) allowed to perform the secondary step of a freeze drying cycle widely independent from duration of this particular step. As a consequence of this particular measure the process economy can be increased, e.g. by a reduction of rejections due to RM levels out of specification.

DETAILED DESCRIPTION OF THE INVENTION

Figure 1:
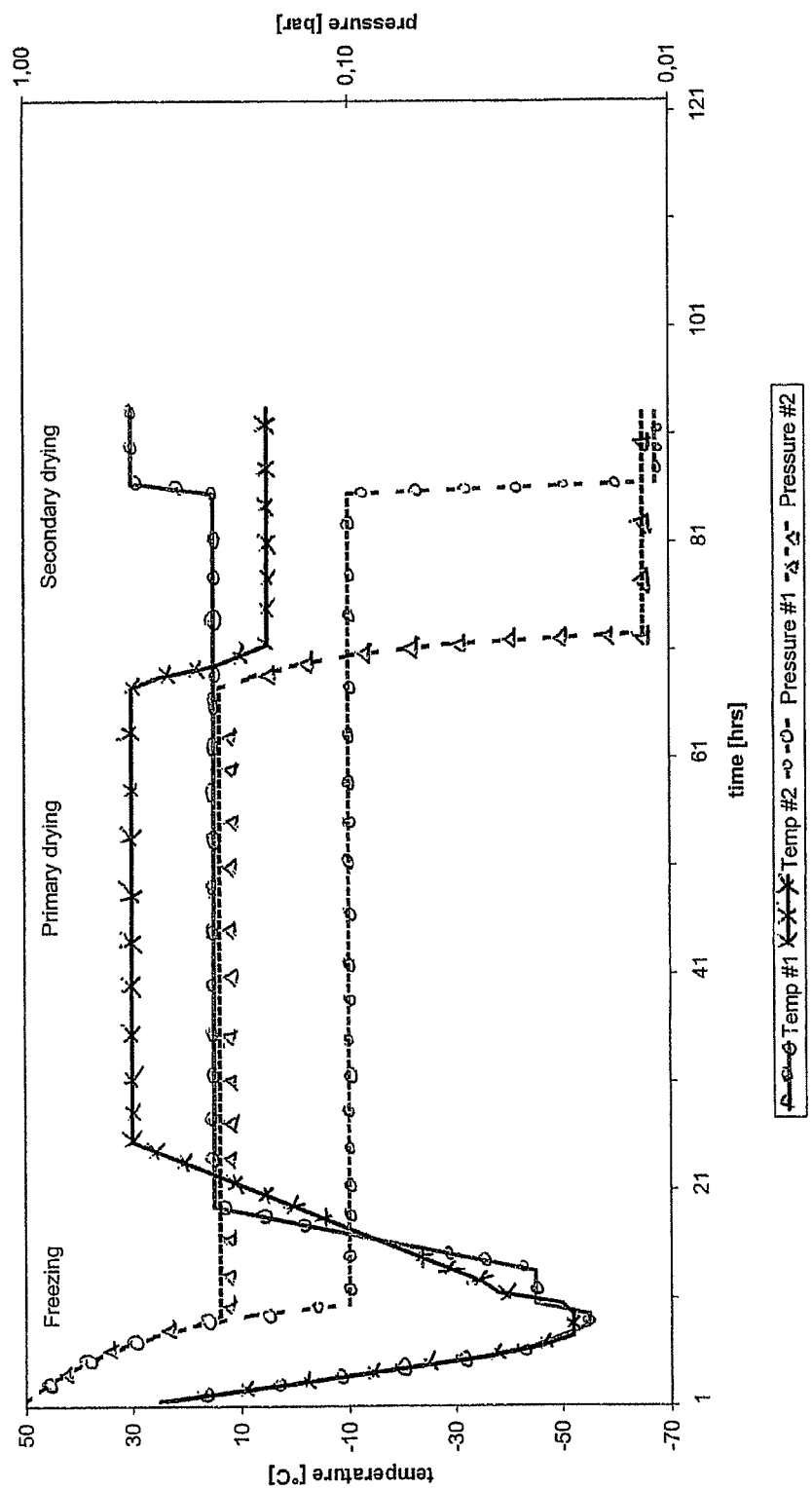
FIG. 1 depicts a schematic drawing of a conventional and the freeze drying cycle of the invention.

The invention discloses a process of freeze drying of an essentially aqueous solution comprising at least one first step having a first temperature and pressure level (i.e. primary drying phase) and at least one second step having a second temperature and pressure level following the first step (i.e. secondary drying phase).

The secondary drying phase is characterized by desorption, which refers to the removal of physically bound water. The amount of desorbable water of a given substance is dependent on the level of energy input typically controlled by heat transfer e.g. via shelves. In conventional freeze drying cycles an excess of energy input is applied, hence the secondary drying phase has to be terminated by time. In contrast, the end point of the process of invention is reached when the desorption approaches zero, that is when under predefined conditions the desorbable water has been removed.

The process of the invention is advantageous since the residual moisture of the formulation can be adjusted to allow further treatment or dedicated use, e.g. thermal treatment for inactivation of chemical or biological compounds, shelf storage and other parameters.

The residual moisture of the formulation is homogenously distributed in the dried samples and prolongation of secondary drying phase does not lead to deleterious effects on the characteristics of the formulation (e.g. overdrying) or a residual moisture content out of specification.

Typically, according to the process of the invention biopolymers such as proteins, polysaccharides, nucleic acids, hormones can be dried. In particular, the biopolymers are pharmaceutical active substances derived from plasma or the corresponding active substances produced by recombinant technology, such as enzymes and their co-factors and inhibitors, hormones, immunoglobulins, growth factors or substances with multi-potent function and activity. In particular the aqueous solution to be freeze-dried contains plasma proteins such as blood plasma, coagulation factors, proteases and cofactors, protease inhibitors, immunoglobulins, albumin and mixtures thereof. Furthermore, the proteins may be one ore more growth factors, hormones, cytokines and mixtures thereof. There is no difference in proteins derived from natural sources or recombinantly produced once or such which were produced transgenically.

When the substances were dissolved in a buffer system, the dried samples also contained buffer substances such as salts used in the biochemical field. If the freeze-dried proteins shall be used in the pharmaceutical field, it is advantageous to freeze-dry in presence of pharmaceutically acceptable salts.

In another embodiment of the invention there may be present salts or other ingredients which ease the later reconstitution of the freeze-dried proteins. Reconstitution may be improved when also detergents are present. Typically, the substances for improving the reconstitution are present in amounts of from 0.001 g/l to 10 g/l, in particular 0.01 g/l to 1.0 g/l.

For example, a human plasma derived protease or cofactor preparation belonging to the coagulation factor family, comprising of the biologically active compound in a buffered salt solution will be cooled to temperatures below 0° C., preferably below the onset of the melting point of the given product as a bulk preparation or in a solid containment like glass vials, ampoules or plastic containments, the latter consisting as a whole or partly of a vapour permeable membrane. To allow closure of the containment under vacuum or defined pressure of inert gases the vials are half closed with stoppers applicable for lyophilisation.

Having the containment in a freeze dryer (in principle consisting of a vacuum chamber with cooled/heated shelves, and a condenser chamber with cooled/heated condenser separated by a valve and the technical equipment to adjust/control temperatures and pressures of the equipment) the chamber pressure is reduced to levels lower than ambient pressure, preferably at ≤0.3 mbar and the condenser is cooled to temperatures below that of the shelves. Subsequently, the temperature of shelves is increased to >0° C., preferably to +20° to +30° C. or higher. Depending of the filling volume or the amount of product the conditions of this phase, i.e. primary drying, are hold for >6 hours or at least until the temperature of the product measured by temperature probes will approximate shelf temperature thus indicating the end of primary drying phase.

Then the secondary drying phase is initiated by lowering the chamber pressure to 0.1 mbar or less, for example 0.01 mbar or less. In contrast to the most commonly applied parallel increase of shelf temperature a set point of the shelf temperature to levels even below those during primary drying is targeted. After ≥4 hours secondary drying phase the freeze drying process is terminated by closing the vials, either at vacuum level as defined for secondary drying or under defined pressure using inert gas, e.g. nitrogen.

FIG. 1 depicts a schematic drawing of a typical conventional freeze drying cycle (Temperature #1, Pressure #1). In contrast to the shelf temperature increase during secondary drying a decrease of shelf temperature according to the invention is applied (Temperature #2, see arrow) allowing to target the RM of a freeze dried substance. The pressure course of the method of the invention is shown as Pressure #2.

According to the invention more homogeneous residual moisture (RM) distribution can be achieved.

The invention is further explained by way of the non-limiting example.

Figure 2:
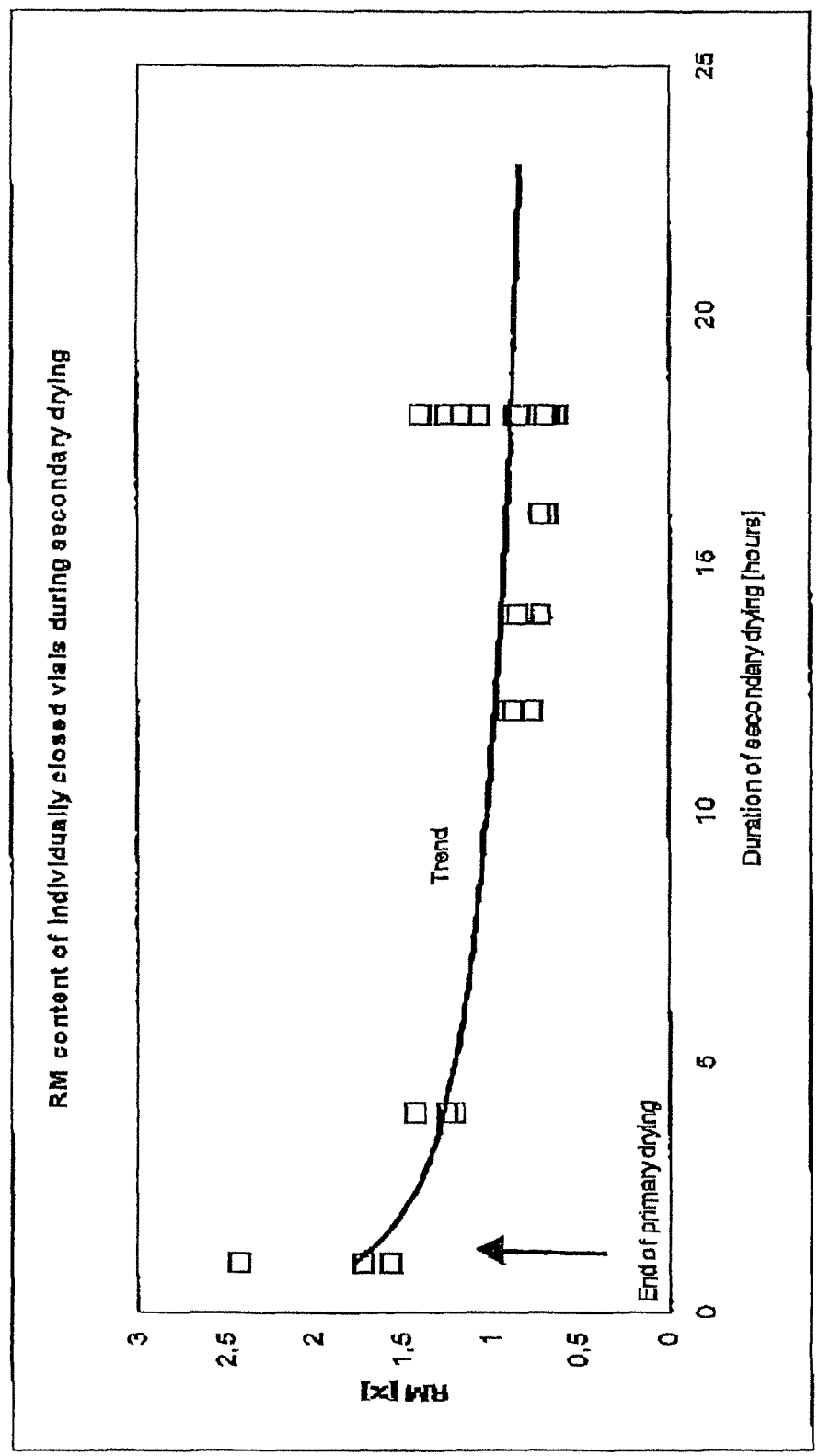
FIG. 2 shows an example of the invention.

A human plasma derived protein component was subjected to freeze drying. After switching from the main drying to the secondary drying phase vials (n=3) were individually closed (by a sample manipulator) at pre-defined time points during secondary drying. At the end of the FD experiment the remaining vials were closed and subsequently all vials were subjected to rest moisture determination. In FIG. 2 the rest moisture values were plotted against time (duration of secondary drying) and the trend line was calculated. It is obvious that at a given shelf temperature the rest moisture of the product reaches a constant level independent on the duration of the secondary drying phase.

In additional experiments using another human plasma derived product the influence of the shelf temperature on the rest moisture content of a given product is listed in the table below. The parameters time and chamber pressure during secondary drying were kept constant while only the shelf temperature was varied. The corresponding rest moisture values of each experiment are also listed. It is obvious that with increasing shelf temperature the mean rest moisture of the product is decreasing. Thus, the control (or limitation) of desorption energy input which is technically equivalent to shelf temperature is an effective tool to adjust a target rest moisture of a given product widely independent of secondary drying time.

| Secondary Drying | Mean reast moisture |
|---|---|
| 3 h at −5° C., 0.01 mbar | 1.14 |
| 3 h at −2° C., 0.01 mbar | 0.92 |
| 3 h at −2° C., 0.01 mbar | 0.98 |

-continued

| Secondary Drying | Mean reast moisture |
| --- | --- |
| 3 h at −2° C., 0.01 mbar | 0.86 |
| 3 h at −2° C., 0.01 mbar | 0.93 |
| 3 h at −2° C., 0.01 mbar | 1.03 |
| 3 h at −2° C., 0.01 mbar | 0.94 |
| Mean value (n = 6) | 0.96 |
| 3 h at +3° C., 0.01 mbar | 0.79 |
| 3 h at +3° C., 0.01 mbar | 0.85 |
| Mean value (n = 2) | 0.82 |

What is claimed:

1. A process of freeze drying an essentially aqueous solution comprising the sequential steps of
   a) subjecting the solution to a primary drying phase at a first temperature and pressure level to obtain a product; and
   b) subjecting the product to a secondary drying phase at 0.01 mbar and a temperature range from −5° C. to +3° C. for at least 3 hours; wherein a limited desorption energy input is applied in the secondary drying phase;
   to obtain a lyophilized product having a predefined target rest moisture in steady-state conditions of 0.79-1.14%.

2. The process of claim 1 wherein the limited desorption energy input applied results in a desorption rate at the target rest moisture of the product approaching zero.

3. The process of claim 1 having a first shelf temperature level and a first chamber pressure level (primary or sublimation drying phase) and at least one second step having a second shelf temperature level and a second chamber pressure level (secondary or desorption drying phase) following the first step, characterized in that in the secondary desorption drying phase at which the desorption rate at the target at rest moisture of the product approaches zero.

4. The process of claim 1, wherein the aqueous solution contains biopolymers such as proteins, polysaccharides, nucleic acids.

5. The process of claim 1, wherein the biopolymers are pharmaceutically active substances.

6. The process of claim 1, wherein the aqueous solution contains proteins selected from the group consisting of plasma proteins such as blood plasma, coagulation factors, proteases or cofactors, protease inhibitors, immunoglobulins, albumin and mixtures thereof.

7. The process of claim 1, wherein the aqueous solution contains proteins selected from the group consisting of one or more growth factors, hormones, cytokines and mixtures thereof.

8. The process of claim 1, wherein the aqueous solution contains recombinantly or transgenically produced proteins.

9. The process of claim 1, wherein the aqueous solution contains prior to drying additionally buffer substances.

* * * * *